（12）United States Patent
Nyholm

(10) Patent No.: US 7,092,483 B2
(45) Date of Patent: Aug. 15, 2006

(54) DIGITAL CAMERA, IMAGING DEVICE AND METHOD FOR DIGITAL IMAGING

(75) Inventor: Kustaa Nyholm, Siuntio (FI)

(73) Assignee: Planmeca Oy, Helsinki (FI)

( * ) Notice: Subject to any disclaimer, the term of this patent is extended or adjusted under 35 U.S.C. 154(b) by 848 days.

(21) Appl. No.: 10/221,058

(22) PCT Filed: Mar. 7, 2001

(86) PCT No.: PCT/FI01/00225

§ 371 (c)(1),
(2), (4) Date: Sep. 9, 2002

(87) PCT Pub. No.: WO01/66012

PCT Pub. Date: Sep. 13, 2001

(65) Prior Publication Data

US 2003/0030721 A1    Feb. 13, 2003

(30) Foreign Application Priority Data

Mar. 7, 2000    (FI)    ................................... 20000521

(51) Int. Cl.
*A61B 6/14*    (2006.01)

(52) U.S. Cl. ........................................ 378/38; 378/98.8
(58) Field of Classification Search .................. 378/21, 378/38–40, 62, 98.8, 167, 168; 250/208.1, 250/370.08, 370.09; 348/36, 207.99, 218.1
See application file for complete search history.

(56) References Cited

U.S. PATENT DOCUMENTS 6,055,292 A * 4/2000 Zeller et al. ................... 378/21

* cited by examiner

*Primary Examiner*—Courtney Thomas
(74) *Attorney, Agent, or Firm*—Wolf Block Schorr & Solis-Cohen LLP

(57) ABSTRACT

The invention relates to a digital camera, an imaging device and a method for dental digital imaging. One sensor is used for tomographic imaging and at least one sensor is used for transillumination imaging. The sensors are arranged to overlap each other. This arrangement provides a multiple use and a relative inexpensive camera compared with the ones using one sensor with a large area. Additionally, it is possible to arrange at least two separate electric connection structures for the different imaging modes. Further, its connection arrangements can be arranged in such a way that the mechanical connection structures of the camera are separated from the electrical connection structures.

44 Claims, 7 Drawing Sheets

Figure 3A:
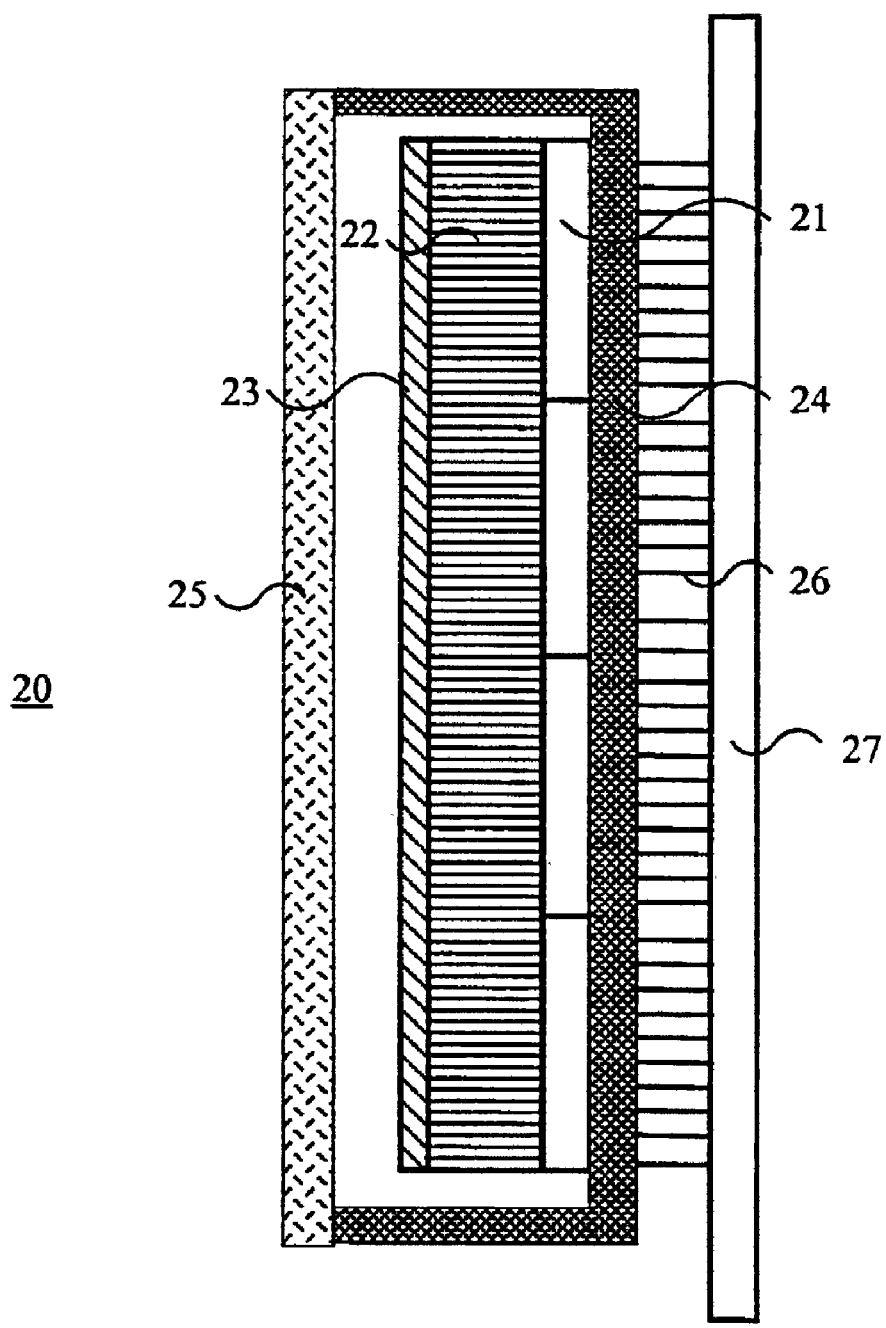

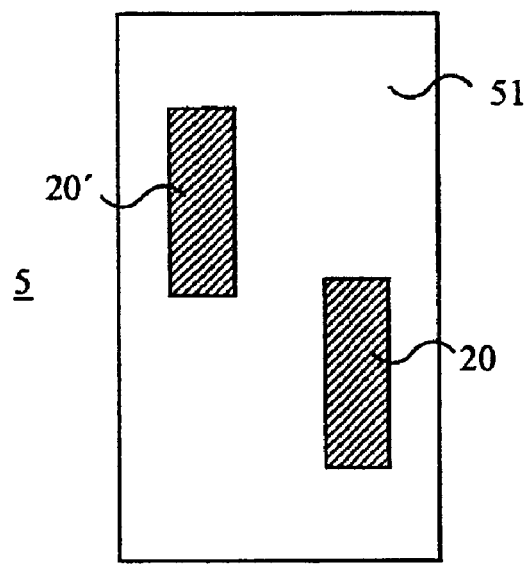
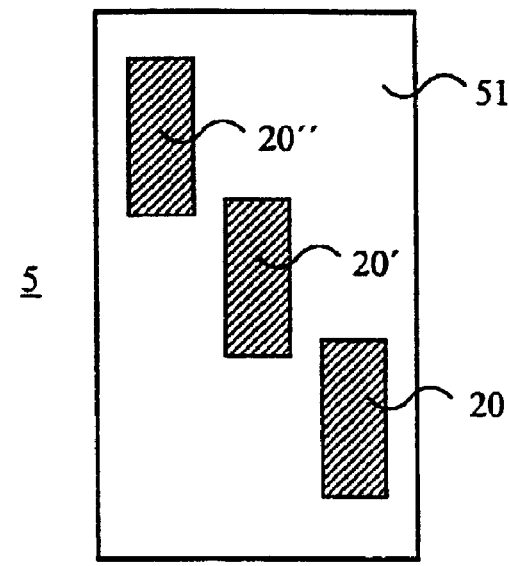
FIG. 3B       FIG. 3C
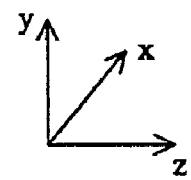
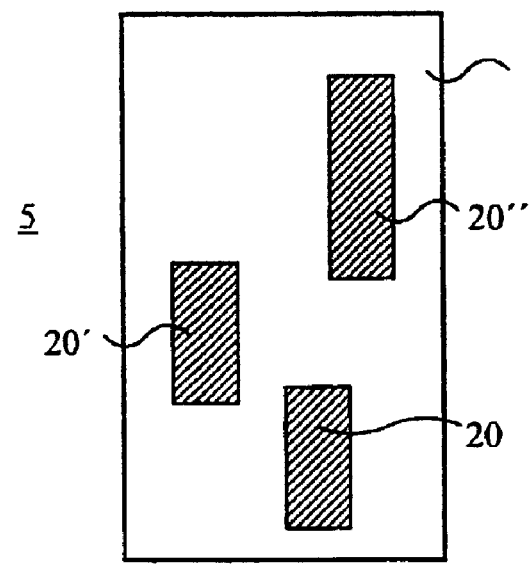
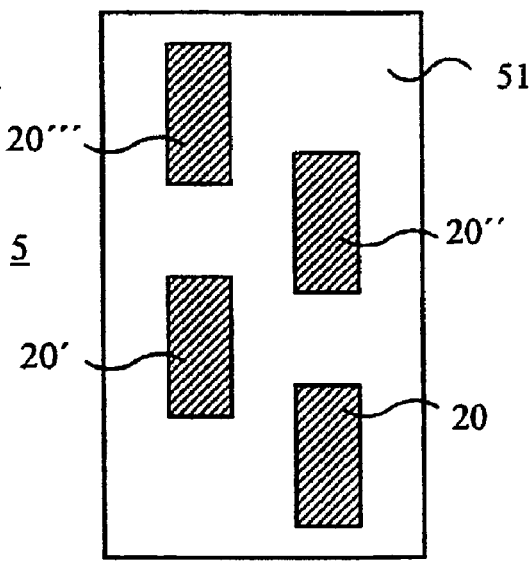
FIG. 3D       FIG. 3E

DIGITAL CAMERA, IMAGING DEVICE AND METHOD FOR DIGITAL IMAGING

This invention relates to a digital camera according to the preamble of claim 1, to an imaging device according to the preamble of claim 23, and to a method according to the preamble of claim 38 for digital imaging.

In particular, one of the objectives of the invention relates to dental panoramic and other tomographic imaging, and to a digital camera and imaging device used in cephalometric imaging, in which the area covered by means for receiving the image information is essentially smaller than the projection of the object to be imaged on the image-forming surface. In this context, the image-forming surface denotes the virtual plane or surface on which the projection of the object to be imaged is formed.

Further, the invention relates to a method for digital imaging in which method the object to be imaged is radiated and the radiation is detected by means for receiving the image information, the area covered by which being essentially smaller than the projection of the object to be imaged on the image-forming surface.

Various tomographic and transillumination imaging methods are used in many kinds of applications. Among others, in the medical and biotechnological imaging applications, it is typical to direct x-ray, gamma, or beta radiation through the object to be imaged and further to the image-forming surface. Digital imaging methods have been developed at the side of the traditional film-based imaging methods, and in these methods semiconductor sensors, such as CDD sensors (Charge-Coupled Device) or CMOS sensors (Complementary Metal-Oxide Semiconductor) are used as image-forming surfaces. Typically, in such semiconductor sensors, x-rays are first converted to radiation the wavelength of which is in the region of visible light but the developing technology is also introducing sensors in which x-rays can be directly converted to electric form.

Despite the many advantages offered by the digital imaging devices, they have not become as generalised as expected in so many visions. The prices of digital cameras have been one of the essential factors having had influence on this. The semiconductor sensors used in the cameras are typically made of silicon and, along with the growth of the size of the sensor, its manufacturing costs per surface area grow exponentially. This is why, in the applications requiring a wide imaging surface, cameras comprising of one semiconductor sensor will become very expensive.

The invention presented in this application has been developed in view of the needs of dental x-ray imaging, and thus, it will be illustrated below primarily in the light of the applications of this field. Naturally, the invention is also suitable for use in connection with many other imaging forms.

The dental x-ray imaging is divided in three main sections, out of which in the so-called intraoral imaging it is typical to image individual, or a few teeth, in the so-called panoramic imaging the dental arch is imaged to a plane as a layer, i.e. as a tomographic image, and in the so-called skull or cephalometric imaging the skull area as a whole is imaged as a transillumination image. Further, many devices used for panoramic imaging are suitable for taking even other cross sectional images of various areas of the dental arch. The present invention is particularly suitable for use in connection with the panoramic and other tomographic imaging forms and with the skull imaging, all of which being typically made by the same imaging device. Particularly in the cephalometric imaging, the need for image information receiving means with large surface area has appeared problematic from the point-of-view of the commercialisation of the digital imaging applications. Taking a skull image with a sensor having a directly matching size with the area to be imaged would require use of tens of times bigger sensors as typically used in panoramic imaging.

As the dental skull image is a transillumination image it is traditionally taken by using so wide a beam and film that the desired area has been able to be imaged as one single shot. On the other hand, in panoramic imaging a tomographic image is typically produced by using a narrow beam and the area to be imaged is scanned by it, whereby the tomographic effect for imaging the desired anatomic layer is created by continuously changing the entry angle of the beam in relation to the object as the beam travels over the area to be imaged. In this so-called narrow beam tomography method, the movement of the imaging means (the radiation source and the image information receiver) is implemented in a controlled way so that the receiver is moving in relation to the beam with a transversal speed corresponding the vertical scanning speed of the beam in the area to be imaged, multiplied with a magnifying factor, i.e. a coefficient that is the relation between the distance from the image information receiver of the focus of the beam (=radiation source) and the distance from the area to be imaged. In this definition, the detector primarily refers to the radiographic film, whereby, in the digital imaging, the movement of the image information receiver in relation to the anatomic layer to be imaged can be replaced by a suitable electric function, as a charge transfer on the surface of the semiconductor sensor. Mathematically, this imaging equation can be presented in the following form:

$$V_F = (L_{FF}/L_{OF}) \times V_O$$

where $V_F$=speed of film transfer, or an electric function by the sensor corresponding to it, $L_{FF}$=distance of film or any respective element from the focus of the radiation source, $L_{OF}$=distance of the object to be imaged from the focus of the radiation source and $V_O$=forward speed, parallel to the image-forming surface, of the beam in the object. Therefore, the precondition to a successful panoramic imaging is that, during the imaging, the respective positions of the means to receive the image information, of the area to be imaged, and the radiation source in relation to each other, continuously remain, as precisely as possible, in compliance with this theoretical imaging equation.

In the digital panoramic imaging, the scanning movement of the beam is followed by a narrow sensor from which the image data is read out during the scan. As the panoramic and cephalometric images have typically been taken by the same x-ray imaging device, it has been a natural idea to use the so-called scanning slot imaging technology also for taking the transillumination images of the skull area (e.g. "Direct digital extraoral radiology of the head and neck with a solid-state linear radiographic detector", McDavid, W. D. et al., Oral Surg Med Oral Pathol 1992; 74:811–7). This is how the sensor surface area needed for imaging has been able to get considerably reduced. In some of such applications, however, the scan has been implemented in a way causing at least theoretical errors in the image, i.e. as the beam is positioned to meet the image information receiver perpendicularly and the scanning of the object is carried out by either conveying the object perpendicularly through the beam, or by positioning the object in a fixed position and by moving the radiation source and the image information receiver with a parallel synchronized movement past the object. These kinds of imaging modes do not produce genuine transillumination images but, as a matter of fact, tomographic images where the size of the tomographic effect depends on the width of the beam used. In addition to this, interpreting of the images obtained in this way is not familiar to the doctors, as their projection geometry is different in the horizontal and vertical directions, thus deviating from the traditional geometry of a transillumination x-ray image.

From the point-of-view of practical applications, use of the same sensor both in the cephalometric and panoramic imagings would be desirable, among others regarding the administration of the camera production and the sensor storage solutions, as the costs of starting the production and, as the manufactured numbers would get larger, the costs per unit, could thus be reduced. In digital panoramic imaging the height of a typically used sensor is, regarding the cephalometric imaging, however, sufficient only in a few special applications, which is why two different sensors have to be manufactured for the market. Therefore, the scanning slot imaging as such does not provide a solution based on which one could manage with only one single sensor.

A feasible possibility as such would be to use a cephalometric imaging sensor in panoramic imaging in such a way that the sensor height would be utilized only partly, but even this solution is problematic from the commercial point-of-view. The sensor that is sufficiently high for cephalometric imaging is more expensive than two panoramic sensors, i.e., with today's prices, the camera needed for cephalometric imaging might cost even more than the rest of the imaging equipment altogether. As typically only about one third of the panoramic devices are provided with means for cephalometric imaging, regarding this and the points presented above, it is very understandable that the digital cephalometric imaging applications have not become significantly more general.

Use of the same digital camera for panoramic and cephalometric imagings has been considered e.g. in the U.S. Pat. No. 5,579,366. This publication primarily discusses one dimensional digital cameras, to the evident idea of using a sensor that is high enough even for cephalometric imaging applications, i.e. a camera that is expensive and overdimensioned from the point-of-view of the needs of mere panoramic imaging. In the scanning cephalometric imaging, a longer sensor than in the panoramic imaging is needed, in any case, whether the imaging scan is made horizontally or vertically.

The actual invention according to the said U.S. Patent Publication concerns the camera interface arrangements that seem to be easy to use as such but that also include potential sources for problems. Use of the same camera in different imaging positions requires its repeated transfer between the panoramic and the cephalometric imaging stations and these measures will always imply a risk of damaging the expensive camera, e.g. as a consequence of dropping it. Often repeated removals and attachments set requirements of their own also to the mechanical, and particularly to the electric interface solutions of the camera. In practice, the problem of the interface solution according to the the publication might prove to be the precise and steady positioning of the camera in the imaging device, which is critical, in particular, in scanning slot imaging.

Also in connection with other imaging applications, different solutions have been developed to solve the surface area/price problem of the semiconductor sensors. Typically in these solutions, sensors covering only a part of the image-forming surface are used, which are then moved or transferred during the exposure, or between, individual exposures. E.g. in the mammographic devices different mosaic or chessboard pattern built sensors have been used, which are then moved between two or several different exposures. Typically, the different modular realisations are expensive and to make them function in practice, too, the combination of the modules has to be carried out with extreme precision—especially when the intention by combining them is to construct a uniform sensor surface based on modules.

The Patent Publication WO 95/12133 presents a modular sensor arrangement, based on the formation of a kind of zig-zag pattern, to be used in different radiographic and tomographic imaging applications. This as such technically excellent solution has not, however, been shown to become a commercial success, at least not in connection with medical imaging—probably at least partly due to the fact that, e.g. a uniform panoramic image cannot be achieved by this kind of a sensor. In the sensor arrangement according to the Publication, the sensor modules are all the time moving, in the direction of the scanning movement, in different stages, i.e. in relation to the rotational centre they are in each moment of time in different positions and are continuously imaging the object from different projections, i.e. they form images based on different imaging geometries. Therefore, such a sensor arrangement creates an image formed of stripes of the different projections, parallel with the scanning movement, where on the borders of them there may be points of incontinuency. In particular, in the (dental) medical radiographic imaging, these kinds of faults in images are not acceptable.

Therefore, the objective of this invention is to develop digital imaging technology to reduce the problems presented above. In particular, the objective is to develop a camera that is relatively inexpensive to manufacture and to acquire, suitable for scanning slot imaging, an imaging device for the use of this kind of camera, and an imaging method based on a corresponding technology. In this way, the investments to digital technology, become more justifiable and the threshold for its introduction lower. The digital technology, among other, will make the doctor's work easier as it enables getting images of better quality, and thus more precise diagnoses, but even saving the pictures and administration of them in electric form—together with the rest of the documentation concerning the patients and the adminstration of the reception.

One of the objectives of the invention is to provide such a camera that it can be used in more than one form of imaging, particularly in both tomographic and transillumination imagings, especially in the same imaging device, and possibly in its different imaging positions. Further, the objective of the invention also is to provide such a method for digital imaging according to which the same camera can be used to take both tomographic images and transillumination images—even of objects of different sizes.

Further, one of the objectives of the invention is to provide a camera the sensor surface of which could simply and with moderate cost be modified, implying that one of the objectives of the invention is to provide this kind of a camera using a modular sensor arrangement. One of the additional objectives of the invention is to provide a modular sensor arrangement for the camera in such a way that the characteristics of the camera can be easily changed, without the need to change its basic structure, when one further additional objective of the invention is to provide the modular sensor arrangement for the camera so that it will be easy to add modules to the camera in order to increase the sensor surface of the camera, or so that the way it is used can be altered so that different imaging modes and imaging of objects of different sizes will be possible with the same camera.

A particular objective of the invention is to provide such a camera suitable for dental panoramic and other tomographic imaging, that can be used, or that can be relatively easily and economically be modified so that it will also be suitable for dental cephalometric imaging.

Further, one of the objectives of the invention is to provide a modular sensor arrangement for the camera so that the camera can be used utilizing only a part of it, especially in tomographic imaging utilizing only one module, that of the sensor arrangement.

One of the additional objectives of the invention also is to implement the sensor arrangement so that the possibly broken individual sensor module could easily be replaceable by a new one, possibly by a module that is identical with the other modules.

A further additional objective of the invention is to provide such a modular sensor system for the camera that the sensor surfaces of the modules and/or the circuit boards belonging to the modules can be positioned also on different levels.

One of the special objectives of the invention is to provide an imaging device in which the same camera according to invention can be used for both tomographic and transillumination imaging, in particular, for both dental panoramic and cephalometric imaging.

Further, one of the additional objectives of the invention is to provide such an imaging device whereby a camera according to the invention can easily and safely be moved from one imaging station to another and positioned precisely in its correct imaging position.

Further, one of the additional objectives of the invention is to implement the camera connection arrangement so that it will consist of at least two structurally different connectors, to connect the camera correctly to its imaging stations for at least two different imaging purposes.

Further, one of the additional objectives of the invention is to provide such an imaging device in the imaging positions of which, designed for at least two different imaging purposes, there are structurally different connecting arrangements for connecting the camera to the imaging device.

Further, one of the additional objectives of the invention is to utilize the connection arrangements of the camera to direct the image information received from certain modules of the camera out from the camera via signal paths exclusively assigned to these modules—in particular, to direct the image information from one module for tomographic imaging out from the camera via a connection arrangement exclusively suitable for a tomographic imaging station.

One of the additional objectives of the invention is to realize the usability of the camera in more than one point of use so that the removal and connection of it would include as few risks as possible for damaging the camera itself, as well as its connecting structures.

Further, one of the additional objectives of the invention is to realize the connecting arrangement of the camera so that its electric connecting parts would be as little vulnerable as possible to mechanical stress that might, in time, damage them and lead to intermittent power contact failures, or even to a permanent failure.

Further, one of the additional objectives of the invention is to realize the connection arrangement of the camera so that it can be positioned to its imaging station relatively simply but in the same time as precisely and for being as non-movable as possible.

Further, one of the additional objectives of the invention is to realize the connection arrangement of the camera so that it will ensure a stable and safe mounting of it in the imaging device, in order to minimize the electrical safety risks that could be caused by e.g. unusually strong external forces upon the camera. These forces can be caused by e.g. stumbling on the camera so that the connection structures would bend and cause shortcuts and thus potential damages to the imaging device and the camera, or even personal injuries as a consequence of an electric shock.

Further, one of the additional objectives of the invention is to provide such an imaging device where the connection arrangements intended for the camera have been realized by using separate mechanical and electric connection structures.

Further, one of the additional objectives of the invention is to realize the connection arrangement so that its mechanical and electric connection structures have been separated from each other, e.g. placed physically on different surfaces of the camera housing.

Further, one of the additional objectives of the invention is to realize the connection arrangement so that fixing of the camera will take place in a compulsory sequence of—positioning—locking of the mechanical connection—electric coupling.

The essential characteristics of the invention have been presented in detail in the attached claims. One of the main characteristics of these is a modular sensor arrangement of a digital camera that consists of, in view of sensor surfaces or their projections on a certain plane, in particular, the point projections in relation to the focus of the radiation source, an overlapping assembly formed by at least two sensor modules—or of a structure including at least the first module, and with means arranged for connecting at least another module functionally to the structure to provide this kind of an assembly; whereby the first module has been arranged to be used for scanning tomographic imaging, and whereby this said module has been arranged to be available for scanning transillumination imaging together with at least another sensor module. In the same way, in the method according to these characteristics, particularly one module unit of the modular sensor assembly is used for tomographic imaging, whereby this same module, together with at least another module belonging to this sensor assembly, is also used for transillumination imaging, whereby imaging of even larger areas than the areas that can be imaged by this first module will become possible.

In particular, the overlapping module assembly according to this invention means a sensor arrangement whereby the sensor modules have been positioned, in relation to each other, in an overlapping position so that considering the sensor surfaces of the sensor modules, or their projections on the plane formed by the axles y, z of a right-angled set of coordinates x, y, z, whereby a projection here indicates, in particular, the point projection which is imaged to said plane via the focus of the radiation source used in the imaging and the said sensor surface, each of them covers a different area on this plane, and that, when proceeding in the direction of the axle y, the projection, or the said point projection of the sensor surface, of each subsequent sensor surface placed on the plane formed by the axles x, z, will cover a different area from the previous projection, and that the projection, or the said point projection of the sensor surface, of each subsequent sensor surface placed on the plane formed by the axles x, y, will meet that of the previous projection—possibly by at least partially covering the same area.

The modular structure according to this definition can therefore be implemented so that, when proceeding in the direction of the axle y, each subsequent projection, on the plane formed by the axles x, z, covers a different area from the previous projection so that the borders of these areas meet.

When the camera with the sensor arrangement according to the invention is positioned in the imaging device using scanning slot technology according to this invention, the direction of the scanning movement of the beam is the direction of the axle z of the definition above.

Thus, the sensor assembly can consist of only the first sensor module used for tomographic imaging and, in addition to this, the means, such as the space required and the means attached to it for connecting at least one another sensor module functionally to this arrangement, in order to form an overlapping modular structure.

Figure 1:
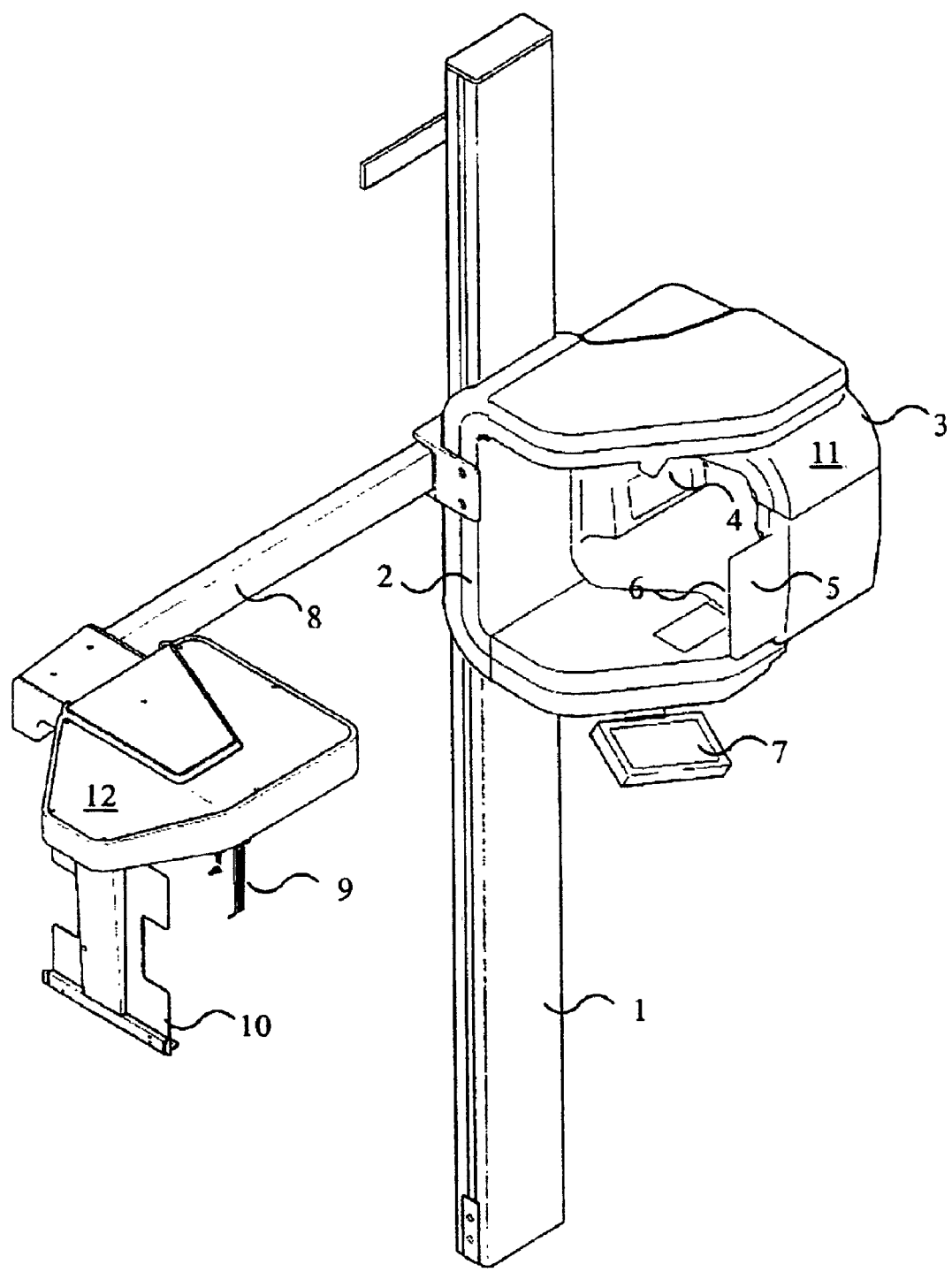
Figure 2:
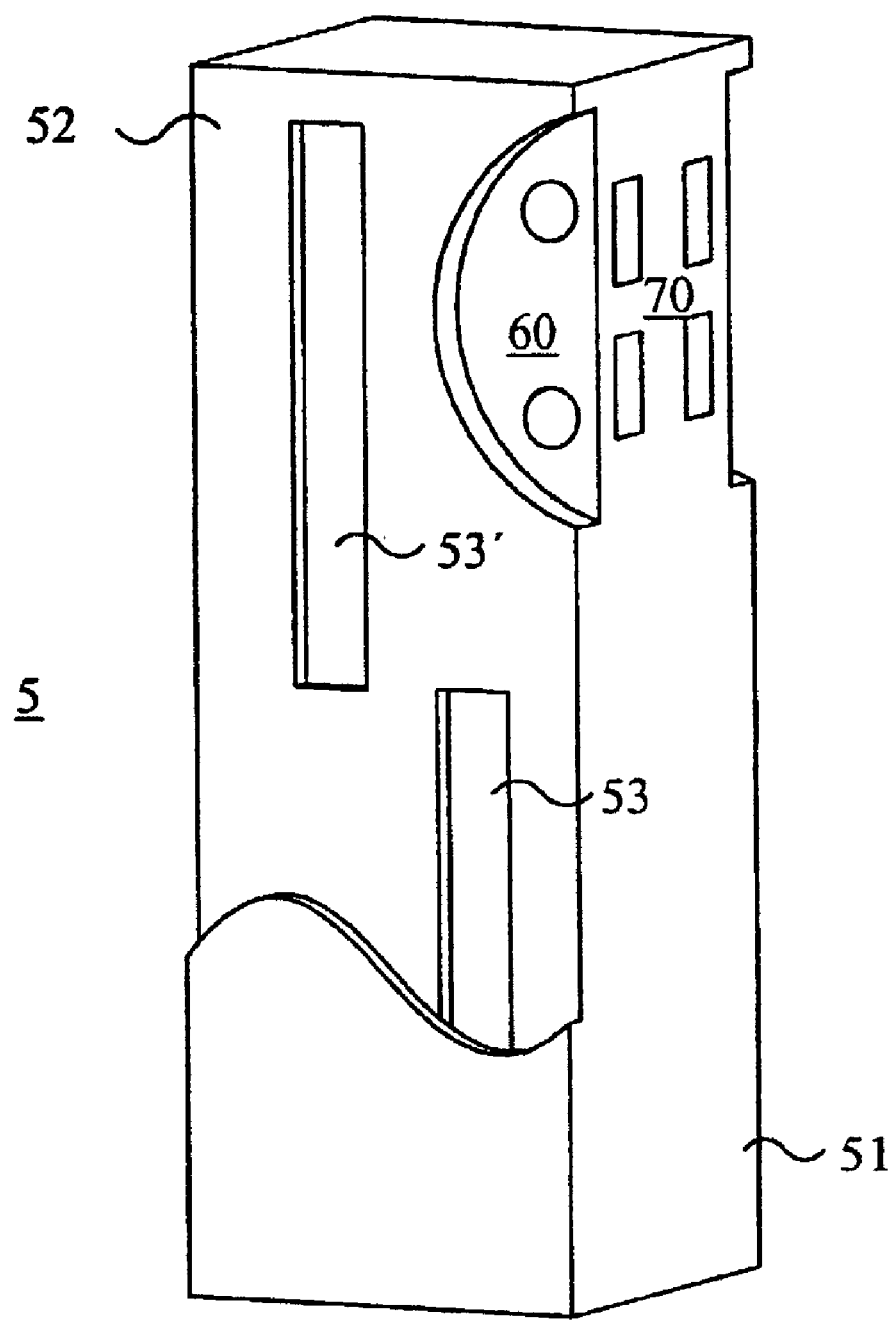
Figure 4:
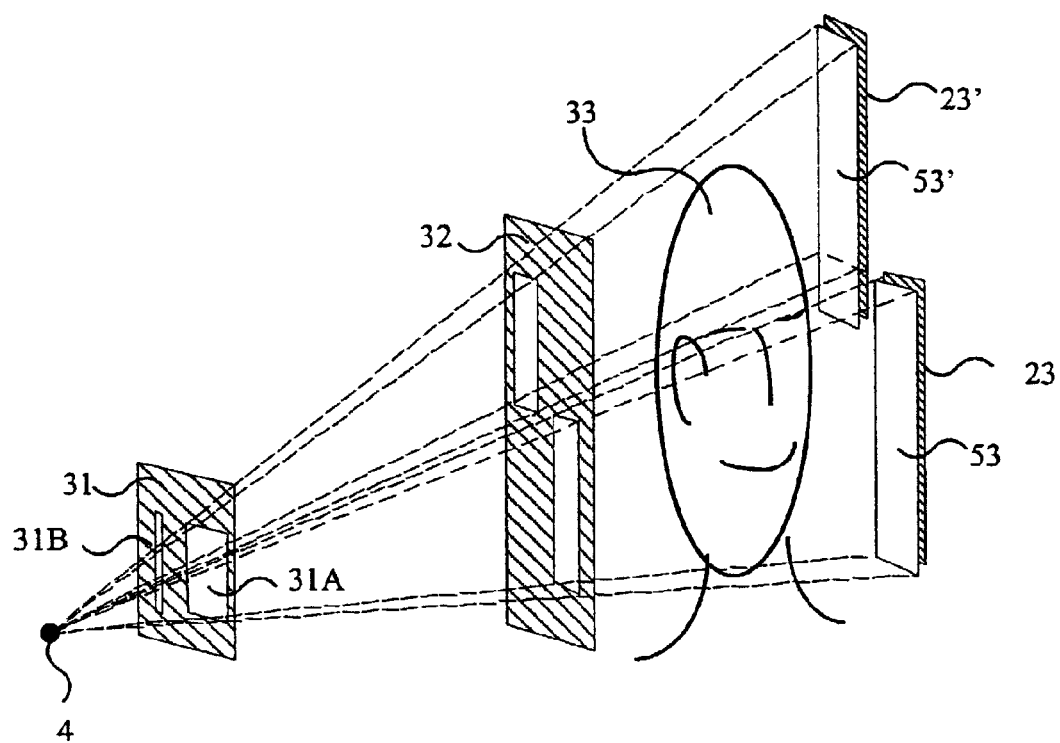
Figure 5B:
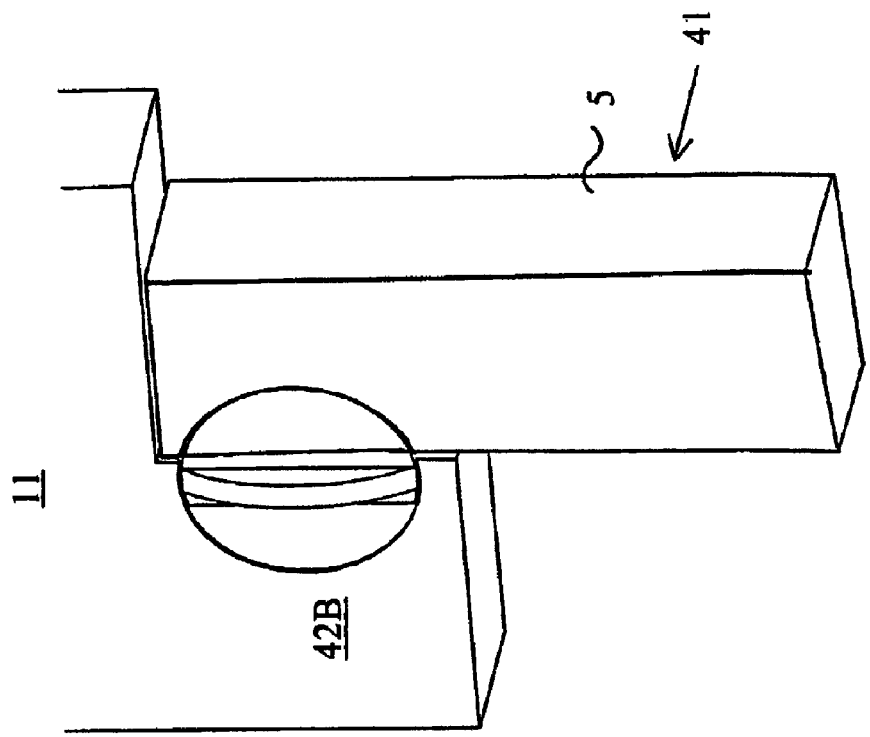
Figure 5A:
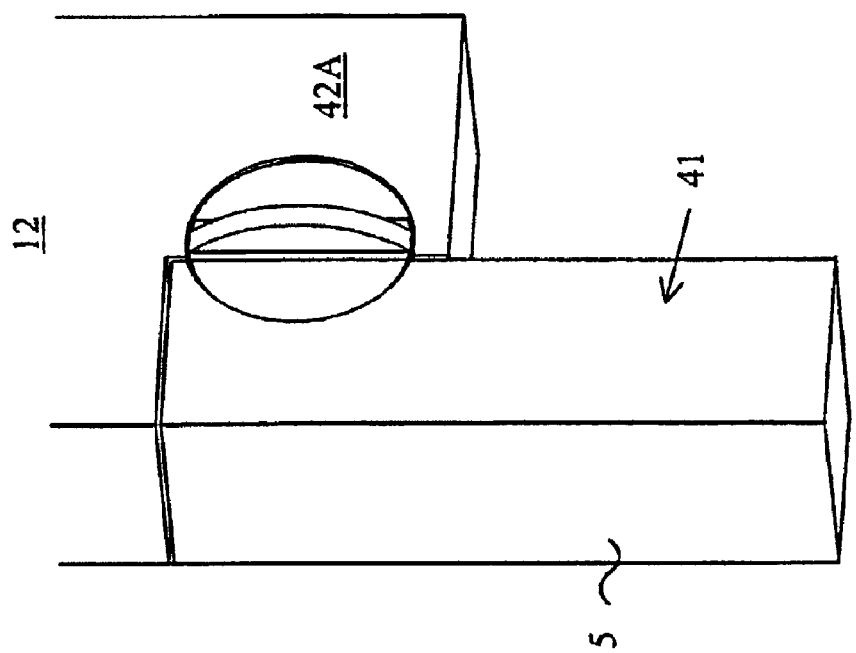
Figure 6:
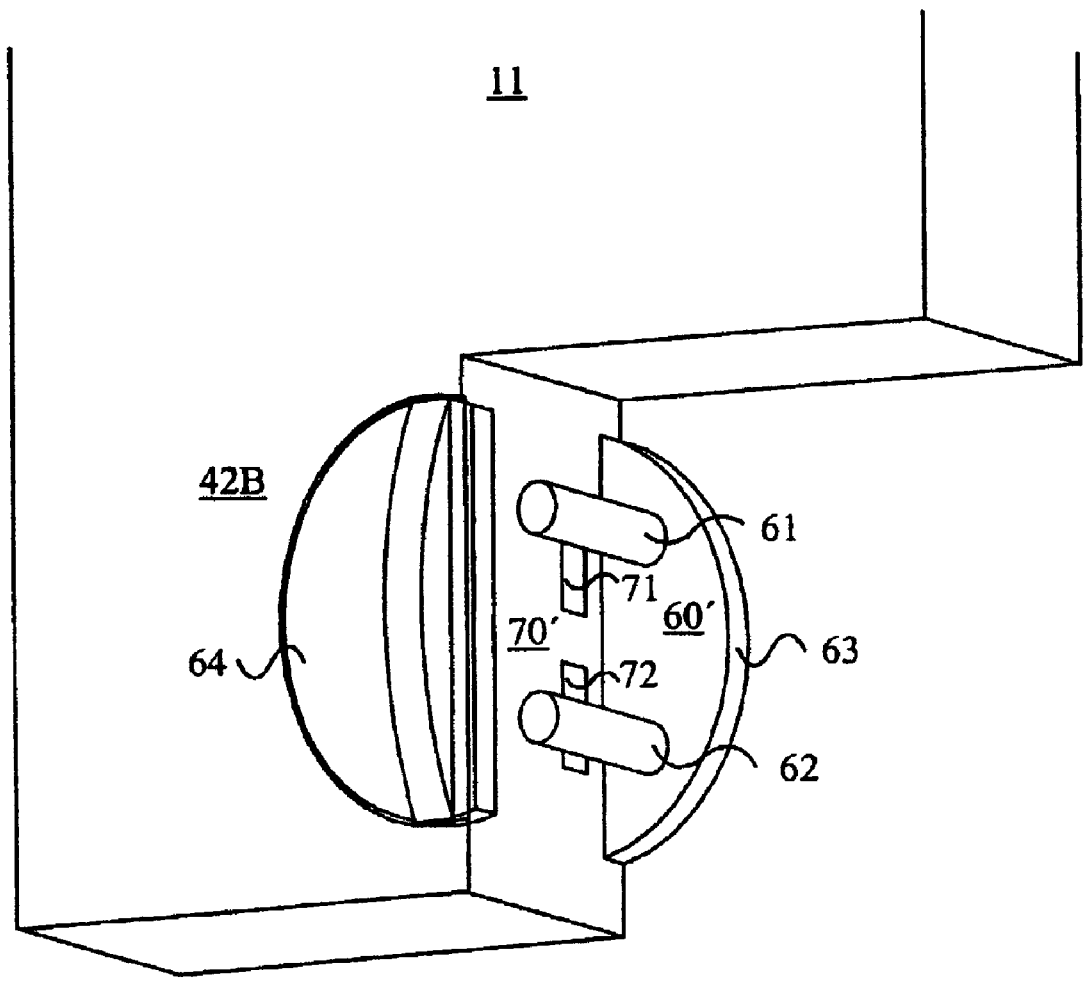

In the following, the invention will be described in more detail, using its preferred embodiments and referring to the attached figures, out of which FIG. 1 shows a typical traditional panoramic and cephalometric imaging device, FIG. 2 shows a structure of a camera housings according to the invention, FIGS. 3A–3E show some sensor module arrangements according to the invention, FIG. 4 shows a collimator system according to one preferred embodiment of the invention used to limit the beam of an imaging device, FIGS. 5A and 5B show one way according to one preferred embodiment according to this invention to connect the camera to the panoramic and cephalometric imaging device, and FIG. 6 shows a camera holder-connector structure in an imaging device according to one preferred embodiment according to this invention.

FIG. 1 shows one typical, traditional film-based panoramic and cephalometric imaging device comprising a body part 1, another body part 2 movably attached to it, with further a suspension arm 3 movably attached to the second body part 2, at the essentially opposite ends of which the radiation source 4 and the image information receiver 5 used in panoramic imaging are located. In the device according to FIG. 1, this image information receiver 5 is a film cassette, but it could also, respectively, be a digital camera attached to the suspension arm 3. In addition, positioning means for the object to be imaged are also typically used in panoramic imaging; their position in FIG. 1 is referred to by reference number 6. To control the functions of the device, it also typically comprises a user interface 7.

To the device according to FIG. 1 are attached means for taking cephalometric images, when it also comprises another suspension arm 8 with positioning means 9 for the object to be imaged in cephalometric imaging attached to it, as well as means 10 for positioning and attaching the image information receiver, which in the device according to FIG. 1 is a film cassette.

In addition, considering the digital application of this kind of device, a panoramic 11 and respectively a cephalometric 12 imaging station of the camera 5 have been indicated by reference numbers 11 and 12 in FIG. 1. These imaging stations will be later referred to in connection with the embodiments of the invention according to FIGS. 5 and 6.

When using the imaging device shown in FIG. 1, the object to be imaged is positioned either in a desired tomographic imaging position, in the area indicated by reference number 6, between the radiation source 4 and the image information receiver 5, or in a desired cephalometric imaging position, by the positioning means 9 used in the cephalometric imaging. In tomographic imaging, a layer of the desired anatomy is imaged by moving the radiation source 4 and the image information receiver 5 in a controlled way on the essentially opposite sides of the object to be imaged so that at the same time the area to be imaged is scanned by a narrow beam. On the other hand, for cephalometric imaging, the radiation source 4 is positioned to direct the beam towards the positioning means 9 used in cephalometric imaging, and further towards the image information receiver not shown in FIG. 1. The traditional film-based devices have typically had to be constructed so that the structures that remain between the radiation source 4 and the cephalometric imaging station 12, as the holder structures of the panoramic film cassette 5, or the like, have had to be moved aside when the device has been changed from panoramic imaging mode to cephalometric imaging mode. In particular, in applications using the same digital camera 5 this problem can simply be solved by producing such a panoramic imaging station 11 of the camera 5 that removal of the camera 5 is sufficient to leave a free path for the beam towards the camera 5 moved to its cephalometric imaging station 12.

FIG. 2 shows a structure of a camera housings 51 of a digital camera 5 according to the invention. In this embodiment of the invention, respective apertures 53, 53' matching the form of one of the sensor module arrangements according to the invention have been arranged to the actual housing part of the camera 5, which is covered by an upholstery surface which is permeable to the radiation used for imaging. In addition, camera 5 comprises means 60 for positioning and mechanical fixing of the camera 5, to be later shown in more detail in connection with FIG. 6, and means 70 for electric connection of the camera, which means can be implemented so that there are separate connecting means in the camera, on one hand for different imaging modes, and on the other for electrical and mechanical connections of the camera to the imaging device.

FIGS. 3A–3E show some of the sensor module arrangements according to the invention. In this context, by sensor module is meant any structure forming an essentially uniform sensor surface. The sensor module 20 may e.g. have the structure shown in FIG. 3A, of the sensor structure 21 formed by four CCD microchips, optical fibre 22, scintillating material 23, housing 24 of the sensor structure 21, cover 25 and a printed circuit board (PCB) 27, or the like, coupled to this structure by electric interface surfaces 26, but it may also consist of, e.g., a single monolithic CCD chip.

The sensor module arrangement according to the invention may be implemented in innumerable different ways out of which some have been shown in FIGS. 3B–3E. These figures show the structure of camera 5 seen from the direction of the focus of the radiation source, when the radiation containing image information is directed via the apertures 53, 53' of the camera housing 52, essentially corresponding to the form of the sensor module arrangement of camera 5, to the sensor modules 20, 20', 20", 20''' that have been placed on the opposite inner wall in relation to the apertures 53, 53'0 of the camera housing. A right-angled set of coordinates x, y, z according to the definition used above has been added to the FIGS. 3B–3E, where the direction of the axle z is the same as the direction of the movement of the camera, i.e. the scanning direction of the beam, when the camera is used for scanning slot imaging.

FIG. 3B shows the simplest embodiment, consisting of two modules 20, 20', of the sensor module arrangement according to the invention. With a camera 5 consisting of this kind of a structure one is able to take a tomographic image using one module 20, and a larger transillumination image by using also the other sensor module 20' positioned in overlapping relation to the first module 20. The stripe-forming effect encountered in tomographic imaging, where at any moment of time during the imaging scan the sensors are at different stages, can be controlled without problems in transillumination imaging. When the focus of the radiation source and the object to be imaged are held stationary and the scanning movement of the beam is implemented by collimators limiting the beam, the modules moving synchronized with the scanning movement form a true transillumination image, each of them at a certain stage of the scanning movement, i.e. e.g. when using the sensor arrangement according to FIG. 3B, when the modules pass the object from left to right, the upper part of the transillumination image will be completed later than the lower one. Even a long distance between the modules 20, 20' in the direction of scanning movement is not problematic from the point-of-view of the formation of the final integrated image but, naturally, e.g. due to the possibly uneven radiation output of the radiation source 4, or regarding the physical dimensions of the camera, this distance should, however, be left as short as will be reasonable, regarding the other solutions of the camera arrangement. And, as in all slot imaging applications of this type, it would also be preferred, in view of the object not to move, to be able to have as short imaging time as possible, i.e. to keep the distance in between the modules scanning direction as short as possible for this reason, too.

If the projections of modules 20, 20', on the plane formed by axles x, y at least partly cover the same area this will not cause any problems in the formation of a transillumination image, as the overlapping parts can be integrated by the image processing methods evident to those professed in the art, to appear as if they had been taken by one sensor. The partial images can be combined e.g. so that the image information corresponding to the part of the object that has possibly been imaged more than once, due to the overlapping of the sensor surfaces, is either removed from the information produced by all the modules except one, or, in particular, so that all of the information received is used in forming the image and the part having been imaged more than once is scaled to correspond the image information that would have been received from only one sensor module. On the other hand, overlapping is also useful regarding the fact that then there will certainly not be left any gaps between the partial images formed by the separate modules. In some special imaging modes it may even be appropriate to arrange two ore more modules to image, even totally, the same area, i.e. to arrange the modules so that, according to the definition used above, the projections of the sensors cover the same areas on the plane formed by the axles x, y.

According to the invention, the camera 5 may also include three, four, or even more sensor modules to form e.g. an over-lapping line according to FIG. 3C, a structure formed by sensor modules of different sizes according to FIG. 3D, or a structure formed by two columns according to FIG. 3E.

Then, FIGS. 3D and 3E illustrate the possibility that, according to the definition used above, when proceeding in the direction of the axle y, the border of the area covered by each successive projection on the plane formed by the axles x, z can be at a distance in different directions from the border of the area covered by the previous projection, compared with the previous projection and the one before it, and that these projections may cover, partly or even totally, the same area. This kind of covering the same area cannot, however, be present when proceeding in the direction of the axle y for any two successive projections.

FIGS. 3B to 3E only show some simple basic structures that cap be combined and extended in many different ways within the basic idea of the invention. Further, according to the invention, the sensor module arrangement can also be realized e.g. by arranging the modules 20, 20', 20", 20''', and, in particular, their surfaces 23 receiving the image information, on different planes, i.e. at different distances from the focus of the radiation source. This can be realized e.g. by using connecting surfaces 26 of different lengths. On the other hand, using connecting surfaces of different lengths, it is possible to create a structure where the sensor surfaces are at the same level but where the printed circuit boards 27, or the like, are at different levels. These types of arrangements allow more latitude for the implementation of the electronics arrangements of the camera. The marginal magnification error caused by the position of the sensor surfaces at different distances from the objects to be imaged can, if desired, be corrected e.g. by the image processing methods known as such.

In order to achieve as effective sensor surface as possible in transillumination imaging using the sensor module arrangement according to the invention, it would be preferred to leave the possible overlapping portion of the sensor surfaces, naturally even for cost reasons, as short as possible. In principle, the sensor module arrangement could be realized so that, according to the definition used above, the projections of the sensor surfaces on the plane formed by the axles x, y, would not overlap at all, i.e. that the distance between them would be zero. A so precise physical positioning of the modules is, however, technically more difficult to achieve than e.g. an arrangement where the modules are positioned at least a little overlapping and the possible extra overlapping will be taken into account in the imaging process, e.g. by using a suitable collimation of the beam. Furthermore, an overlapping of the size of at least one row of sensor pixels is preferred also because the combination of images is then more easily feasible, using means offered by many as such known electronic and/or image processing software solutions. Especially if the effective height of the sensor arrangement does not belong to the critical development criteria, the use of overlapping and its optimal magnitude can be considered in the light of any particular characteristics of the respective application.

Regarding the needs of dental imaging, it is preferred to arrange the module used for tomographic imaging as the lowest module of the sensor module arrangement, as in all other cases especially the imaging of the lower jaw onto the panoramic image is difficult to arrange. In these type of applications, it is also preferred to implement the sensor module arrangement according to the invention so that two identical modules, possibly in overlapping positions, are used, and the physical and electronic arrangements of the camera are implemented so that the modules can be easily removed and/or connected to the camera. Expressed more precisely, this means that it will be possible, in the first stage, to arrange in the camera housing only the module needed for tomographic imaging, and the physical space needed for the transilllumination imaging module plus the necessary means for its positioning and functional connection to the camera. In this way, a panoramic camera is provided with a relatively inexpensive acquisition price, and to which, however, another module needed for cephalometric imaging can later be connected in a simple way. In addition to this, thus a damaged module can easily be replaced by a new one and if the damaged module happened to be one used only for cephalometric imaging, the camera can still be used for panoramic imaging purposes even during the time the acquisition of a new module takes. The price of this type of a panoramic camera can be made to match the price of a conventional panoramic camera, i.e. the camera will be significantly cheaper—due to its smaller sensor surface— than a panoramic camera consisting of one sensor module that could as such also be used for cephalometric imaging. In addition, even price of a camera according to this invention, extended suitable also for cephalometric imaging, consisting of two relatively small sensor modules will, however, remain clearly lower than that of a one module camera of comparable size. Even in a more general consideration, a sensor arrangement according to the invention can thus be realized so that, for whatever single module or several modules used only for transillumination imaging, only the physical space and the necessary means for connecting the module functionally to the camera are arranged to the camera housing, in which case the sensor arrangement can by simple connection measures be arranged to form a larger overlapping modular structure.

According to the invention, there are numerous ways to remove or discard the signal produced by other modules than that used for tomographic imaging from the image information used for creating the tomographic image. E.g. the electronics arrangements of the camera can be implemented so that the signal path to the transillumination imaging modules can be cut, or so that the image is formed, or the image data is transmitted from the camera to separate image processing means only from the signal received from the tomographic imaging sensor. The non-desired information can be sorted out and removed by using electronics arrangements, known as such, e.g. in the logic circuit of the camera, or later by image processing methods, known as such. In addition or besides to these arrangements, it is also possible to proceed so that the collimation arrangement limiting the beam of the imaging device is implemented so that, when the imaging device is used for tomographic imaging, the access of radiation to other sensor modules is blocked.

Further, taking into consideration certain preferred embodiments to be presented later, one possible solution is to arrange two sets of separate electric connection means for the camera, in which case the signal paths can be arranged so that one connecting element will be in connection only to the tomographic imaging sensor module and the other both to the tomographic imaging sensor module and at least to one transilluminaton imaging sensor module—or then at least to one of the connection means arranged for this type of module. Thus, when the first mentioned electric connector is used for attaching the camera to the tomographic imaging position, automatically, only the image information produced by the tomographic image sensor module is obtained via this connector, as desired.

The final formation of the image may be done in ways known as such, e.g. by connecting the imaging device to a computer, whereby the memory and the processing means of the computer can be utilized. The processing means can also be realized by e.g. a dedicated ASIC circuit (Application Specific Integrated Circuit), connected to memory means, e.g. RAM memory. Naturally, and as already partially described above, many measures of the image information processing can already be carried out in the camera, e.g. specifically in the ASIC circuit arranged to the camera. The formation of the final image information as such is well-known technology to those professed in the art, and a more detailed description of it is not necessary for the implementation of the invention. In principle, the camera may be made by arranging all means required for the image formation in the camera itself when it could be connected directly to the display device.

In the implementation of the invention, it is possible to utilize the CCD sensor technology known as such, having shown to be very useful in e.g. panoramic imaging. On the other hand, one interesting alternative also is the use of a newer technology based on CMOS sensors and direct detection of radiation, as with them certain advantages can be obtained as compared to the traditional semiconductor sensors. The CMOS sensor technology as such enables, due to its so-called parallel bus type data transfer system, a faster transfer of image information, and with sensors based on direct detection an even better resolution is achieved than with the traditional semiconductor sensors, when there are no scintillating and optical fibre structures reflecting light also to non-desired directions. The sensitivity of the sensors based on direct detection is better, too. The CMOS technology is the most commonly applied semiconductor technology and, because of this, the availability of CMOS circuits is good and their manufacturing costs are being reduced by the technical development.

One of the sensor technologies based on direct detection of radiation has been described in more detail e.g. in the Patent Application Publications WO 95/33332 and WO 97/20342. It is not possible to perform a charge transfer function (Time Delay Integration=TDI) with this type of a sensor, nor is there any simple way to construct such a function to it. However, this type of a sensor can be used in these imaging modes by forming the image so that an image of the object is produced every time the object to be imaged, or the sensor, has moved about one pixel forward, and by adding these images to each other so that they are, at the same time, overlapping a corresponding distance in relation with each other.

FIG. 4 shows one preferred embodiment of the invention for a collimator arrangement for limiting the beam, which in the situation shown in the figure has been arranged to be ready for use in cephalometric imaging. In cephalometric imaging the beam received from the radiation source 4 is first limited by a primary collimator 31 (collimator opening 31A) placed in the vicinity of the radiation source 4, and before the object to be imaged 33 by another collimator 32 placed to a sufficient distance from the focus, which will limit the beam to essentially match the form of the areas 53, 53' the camera housing, which are permeable to radiation. The scanning movement of the beam is realized by the movement of the collimators and the camera is moved synchronized with this movement. If the sizes of the active surfaces 23, 23' of the sensor modules 21 and of the areas 53, 53' permeable to radiation, especially their overlapping, are arranged to be larger than the effective sensor surface 23, 23' required in the respective imaging, with a suitable limitation of the beam it will be possible to prevent the unnecessary direction of radiation through the object to be imaged 33 twice, to the area of the sensor surface not to be utilized in image formation, and the image information of the area left outside the beam can be removed before the partial images are combined.

Panoramic imaging can be realized in a manner known as such by the structure according to FIG. 4 by positioning the aperture 31B, intended for panoramic imaging, of the primary collimator 31 in the essential vicinity of the radiation source 4 to limit the beam to match the conventional beam used in panoramic imaging, i.e. to essentially match the aperture 53 of the camera housing.

The FIGS. 5A and 5B show one of the preferred ways to attach the camera 5 according to the invention to the imaging device. In the solution according the figures, the camera 5 can be considered as positioned e.g. to its cephalometric imaging station 12 in FIG. 5A and to its panoramic imaging station 11 in FIG. 5B. In FIGS. 5A and 5B arrow 41 indicates the entry direction of the x-rays to the camera 5, i.e. the camera 5 and the connection arrangements 42A, 42B of the imaging device have been arranged to be of different structure, so that the camera 5 can, on one hand, only be mounted from one direction to the cephalometric imaging station 12, and from the other direction to the panoramic imaging station 11 (compare with FIG. 1). When the said directions have been arranged horizontally according to FIGS. 5A and 5B, moving the camera 5 between the imaging stations 40A, 40B is easy and fast, and at the same time, the danger of dropping the camera 5 unintentionally has been minimized. When positioning oneself to the area between the panoramic imaging station 11 and the cephalometric imaging station 11, 12, the camera is easily removable from one imaging station and attachable to the other imaging station by using a simple horizontal movement. In this way, that critical time for the risk of damaging the camera 5 when it is not safely mounted and secured to the imaging device, is reduced.

Technically, the imaging device according to the invention is, naturally, also possible to realize so that the scanning movement of the beam is made in some other direction than horizontally. Especially, the panoramic and cephalometric imaging devices according to the invention can be made so that the scanning movement of the cephalometric imaging is arranged to be done in vertical direction, whereby the sensor module arrangement can be implemented in a somewhat shorter form.

FIG. 6 shows a connection arrangement 60', 70' enabling one preferred embodiment of the invention shown in FIG. 5 to fix the camera 5 according to FIG. 2 to the imaging device. The structure shown in FIG. 6 may be considered to correspond the panoramic imaging station 11 according to FIG. 5B, when e.g. the respective connecting arrangement (60, 70) forming a structural mirror image may be arranged to the cephalometric imaging station 12. The connection arrangement 42B according to FIG. 6 consists means 60' for positioning and mechanical mounting of the camera 5 and means associated with the electrical coupling 70' of the camera. The camera 5 is brought to the imaging station 11 in the direction of the guiding rails 61, 62 that ensure the correct positioning, from the opposite side of their end plate 63. When the guiding rails 61, 62 have penetrated fully into the matching guiding grooves in the camera 5, the fixing of the camera 5 can be secured by turning the locking means 64 to its locking position over the camera housing 51. Additionally, the connection arrangement according to FIG. 6 can also be made so that the electric connecting means 71, 72 are moved to contact the matching elements in the camera not until the camera has been mechanically locked, e.g. with a perpendicular movement in relation to the direction of the positioning movement of the camera, which is realized by a pressing element appearing from below of the locking means 64. Thus, the sensitive electric means can be protected from mechanical stresses by this kind of compulsory operating sequence of positioning—securing the mechanical connection—electric coupling. In particular, this kind of an arrangement enables the realisation of the electric coupling and its switching off without any gliding movements of the connecting means. The connecting arrangement 42B according to FIG. 6 does not cause mechanical stresses to the means 70 involved with the electric coupling of the camera 5 and the imaging device even when the camera is connected to its operational station. The mechanical stresses on the electric connectors are problematic, especially if the duration of them is long, as the connection elements may bend with time, or otherwise be damaged to the extent that the electric contact starts to fail, or even becomes cut off permanently.

As already partly described above, in the solution according to FIG. 6 specifically horizontal rails have been used to reduce the possibility that the expensive camera would slip to the floor unintentionally during its removal and/or mounting. On the other hand, intention in using more than one guide rail, as well as in separating the positioning and the actual locking means to elements of their own, is to ensure the correct positioning of the camera, regarding which in slot imaging, in particular in the direction of the width of the narrow beam, one must especially precise. The solution according to FIG. 6 of separating the actual mechanical connection from the electric coupling also reduces e.g. the imminent danger of shortcuts by unintentional crashes to the camera that could lead to a consequence of damaging the camera, or the imaging device as a whole, or even to fatal danger in the form of an electric shock.

The connecting arrangements 42A, 42B of the separate imaging stations 11, 12 can be realized as structurally different so that the camera 5 can be attached to one imaging station 11 only by using a connection arrangement 60, 70 only compatible with it, and to another imaging station 12 by using another connection arrangement. Thus it can be ensured that the camera 5 will always be connected correctly to each imaging station 11, 12. At the same time, the operational life time of the electric connectors will be increased when the number of times of coupling per connector structure is reduced to half, and even if, despite of the above, one connection arrangement would be damaged, the camera could still be used at least in one of the imaging stations during the time the acquisition of a new camera, or in practice, most likely new connecting means, will last.

As a summary, it can be said that, according to the embodiment of the invention shown in FIGS. 2, 5, and 6, there are structurally different connection arrangements for the tomographic and for the transillumination imaging stations, whereby, respectively, there are two structurally different connection arrangements in the camera, and these connection arrangements consist of separate mechanical connection structures and electric connector elements arranged as independently functioning elements, one for connection for tomographic imaging on one hand and the other for transilluminaton imaging connection on the other. The electric coupling means arranged to the imaging devices are connected to means for moving them in order to move them into contact with the coupling means located in the camera, and when the mechanical connection means are arranged to consist of separate positioning and locking means for the mechanical connection, the camera according to this embodiment of the invention can be attached to the imaging device by one connection arrangement consisting of two separate connection structures only to a certain kind of connection arrangement of the imaging station, and only using a compulsory operating sequence of positioning—securing the mechanical connection—electric coupling.

Although the invention has been described above mainly by using panoramic and cephalometric imaging applications as examples, it can naturally also be used in connection with any other corresponding imaging applications. For example, according to the invention, any radiation that can be detected by semiconductor sensors can be used.

The invention is especially useful in the imaging applications of medical technology where x-ray or gamma ray radiation is typically used, or in biotechnological applications where beta radiation is typically used. Further, the invention can be applied to industrial testing and quality control methods utilizing transillumination.

For those professed in the art, it is evident that, especially with developing technology, the basic idea of the invention is realizable in many ways, and the embodiments will not be limited by the above examples, but they can vary within the scope of protection defined in the attached claims.

The invention claimed is:

1. A digital camera for dental imaging comprising:
   an image forming surface;
   a first sensor module arranged on said image forming surface, said first sensor module being structured and arranged for receiving tomographic imaging information;
   a second sensor module arranged on said image forming surface, said second sensor module being structured and arranged for receiving transillumination imaging information;
   wherein said first sensor module has a bottom edge and said second sensor module has a top edge, said bottom edge of said first sensor terminating vertically below the top edge of said second sensor module.

2. The digital camera according to claim 1, further comprising:
   means for forming an image information signal from said tomographic imaging information received by said first sensor module.

3. The digital camera according to claim 1, further comprising:
   means for forming an image information signal from said transillumination imaging information received by said second sensor module.

4. The digital camera according to claim 1, further comprising means for receiving the imaging information received by said first sensor module and said second sensor module and forming a transillumination image corresponding to an area covered by both of said first and second sensor modules.

5. The digital camera according to claim 1, wherein each of said first and second modules have a sensor surface and each of said sensor surfaces are arranged on a y-z plane of a right angled x, y, z coordinate system, said first and second sensor modules being arranged such that a projection of the sensor surface of the first sensor module taken along the x-y plane intersects with a projection of the sensor surface of the second sensor module taken along the x-y plane.

6. The digital camera according to claim 5, further comprising a plurality of additional sensor modules, each one of said additional sensor modules being arranged such that a projection of the sensor surface taken along the x-y plane intersects with a projection taken along the x-y plane of the sensor surface of a previous one of said plurality of additional sensor modules.

7. The digital camera according to claim 5, wherein a peripheral perimeter edge of an area defined by a projection of the sensor surface of the first sensor module taken in the x, z plane is spaced from a peripheral perimeter edge of an area defined by a projection of the sensor surface of the second sensor module taken in the x, z plane.

8. The digital camera according to claim 1, further comprising:
   at least a third sensor module;
   wherein each of said first, second and third modules have a sensor surface and each of said sensor surfaces are arranged on a y-z plane of a right angled x, y, z coordinate system, said first, second and third sensor modules being arranged such that a projection of each sensor surfaces taken along the x-z plane intersects with at least one other projection of the other sensor surfaces taken along the x-z plane.

9. The digital camera according to claim 8, wherein at least two of said first, second and third modules are arranged in a first column in the x-y plane and the other one of said first, second and third modules is arranged in a second column in the x-y plane.

10. The digital camera according to claim 1, wherein said first and second sensor modules are substantially the same size.

11. The digital camera according to claim 1, wherein said first module is arranged vertically above said second module.

12. The digital camera according to claim 1, further comprising:
    means for operably connecting said camera to a display device.

13. The digital camera according to claim 12, wherein said means for operably connecting said camera to said display device includes a first signal path for transmitting image data to and from said first sensor module and a second branched signal path for transmitting image data to and from said first sensor module and to and from said second sensor module.

14. The digital camera according to claim 12, wherein said branched signal path includes means for combining partial images produced by said first and second sensor modules to produce a transillumination image.

15. The digital camera according to claim 12, wherein said means for operably connecting said camera to said display device includes separate means for mechanically connecting said camera to said display device and means for electrically connecting said camera to said display device.

16. The digital camera according to claim 15, wherein said means for mechanically connecting said camera to said display device includes means for positioning said camera.

17. The digital camera according to claim 12, means for operably connecting said camera to a display device includes structurally distinct first means for connecting said camera to said display device for tomographic imaging and second means for connecting said camera to said display device for transillumination imaging.

18. The digital camera according to claim 17, wherein said first means for connecting said camera to said display device and said second means for connecting said camera to said display device are located on different physical surfaces of said camera.

19. An imaging device for dental imaging comprising:
    a radiation source for producing a radiation beam;
    an imaging station;
    a collimator structure for limiting the beam received from the radiation source;

means for mounting a camera;

means for positioning the object to be imaged;

means for receiving image data from the camera comprising a first sensor module arranged on an image forming surface, said first sensor module being structured and arranged for receiving tomographic imaging information and a second sensor module arranged on said image forming surface, said second sensor module being structured and arranged for receiving transillumination imaging information;

wherein said first sensor module has a bottom edge and said second sensor module has a top edge, said bottom edge of said first sensor terminating vertically below the top edge of said second sensor module whereby portions of the first and second sensor are partially overlapping.

20. The imaging device according to claim 19, further comprising:

means for forming an image information signal from said tomographic imaging information received by said first sensor module.

21. The imaging device according to claim 19, further comprising:

means for receiving the imaging information received by said first sensor module and said second sensor module and forming a transillumination image corresponding to an area covered by both of said first and second sensor modules.

22. The imaging device according to claim 19, wherein each of said first and second modules have a sensor surface and each of said sensor surfaces are arranged on a y-z plane of a right angled x, y, z coordinate system, said first and second sensor modules being arranged such that a projection of the sensor surface of the first sensor module taken along the x-y plane intersects with a projection of the sensor surface of the second sensor module taken along the x-y plane.

23. The imaging device according to claim 19, wherein said first module is arranged vertically above said second module.

24. The imaging device according to claim 19, wherein the collimator structure is structured and arranged to enable the limitation of the beam exclusively to the first sensor module during a tomographic imaging.

25. The imaging device according to claim 19, further comprising:

means for taking a transillumination image by carrying out the scanning movement of the beam by keeping the focus of the radiation source steady and by moving the collimation arrangement limiting the beam in a synchronized way with the movements of the camera.

26. The imaging device according to claim 19, wherein said imaging station is a tomographic imaging station, said imaging device further comprising:

a transillumination imaging station; and wherein said tomographic imaging station is arranged nearer to said radiation source than said transillumination imaging station.

27. The imaging device according to claim 26, wherein said collimator structure comprises a primary collimator structure located in the vicinity of the radiation source and a secondary collimator structure located at a distance from said radiation source in the vicinity of said transillumination imaging station.

28. The imaging device according to claim 27, wherein said primary collimator structure is structured and arranged to enable the limitation of said radiation beam to essentially match the form and size of said first sensor module, and said secondary collimator structure is structured and arranged to enable the limitation of said radiation beam to essentially match the overlapping portions of said first and second sensor modules.

29. The imaging device according to claim 26, further comprising:

means for operably connecting said camera to said tomographic imaging station.

means for operably connecting said camera to said transillumination imaging station.

30. The imaging device according to claim 29, wherein one of said means for operably connecting said camera to said tomographic imaging station and said means for operably connecting said camera to said transillumination imaging station comprises separate electrical and mechanical connection means.

31. The imaging device according to claim 30, wherein said separate electrical and mechanical connection means are structured and arranged such that said mechanical connection must be connected prior to a connection of said electrical connection means.

32. The imaging device according to claim 30, wherein said mechanical connection means comprises separate positioning means and means for locking the connection means in a connected state.

33. The imaging device according to claim 30, wherein said camera and said mechanical and electrical connection means are structured and arranged such that during a mounting procedure of said camera the camera must be mounted following a compulsory sequence in which said mechanical connection is connected, said means for locking the connection means is locked, and the said electrical connection means is connected.

34. A method for dental digital imaging comprising the steps of:

arranging a radiation source to emit a radiation beam at an area to be imaged;

arranging a collimator structure to limit said radiation beam;

arranging a sensor assembly such that the same sensor assembly is utilized for taking both tomographic images and transillumination images, wherein said sensor assembly includes a first sensor module structured and arranged for receiving tomographic imaging information and a second sensor module structured and arranged for receiving transillumination imaging information, and wherein said first sensor module has a bottom edge and said second sensor module has a top edge, said bottom edge of said first sensor terminating vertically below the top edge of said second sensor module whereby portions of the first and second sensor are partially overlapping.

35. The method according to claim 34, further comprising:

forming an image information signal exclusively from the information received by said first sensor module.

36. The method according to claim 35, further comprising:

removing said information obtained from said second sensor module to thereby form said image information signal exclusively containing information received by said first sensor module.

37. The method according to claim 34, further comprising:

combining image information received from said first and second sensor modules to form a transillumination image signal.

38. The method according to claim 37, further comprising:

reading image information from different stages of a scanning movement receiving by said first and second sensor modules and then combining said information received from said first and second sensor modules to form said transillumination signal; and removing any duplicate information obtained from both said first and second sensor modules from said transillumination signal to thereby from a complete transillumination image.

39. The method according to claim 37, further comprising:

limiting said beam by said collimator structure before said area to be imaged such that a projection of said beam on said area to be imaged is substantially equal in size to a projection of said first and second modules on said area to be imaged.

40. The method according to claim 34, further comprising:

providing means for operably connecting said camera to said display device including a first signal path for transmitting image data to and from said first sensor module and a second branched signal path for transmitting image data to and from said first sensor module and to and from said second sensor module.

41. The method according to claim 34, wherein each of said first and second modules have a sensor surface and each of said sensor surfaces are arranged on a y-z plane of a right angled x, y, z coordinate system, said first and second sensor modules being arranged such that a projection of the sensor surface of the first sensor module taken along the x-y plane intersects with a projection of the sensor surface of the second sensor module taken along the x-y plane.

42. The method according to claim 34, wherein said first module is arranged vertically above said second module.

43. The method according to claim 34, further comprising:

limiting said radiation beam to match said first module during a tomographic imaging and limiting said radiation beam to match said first and second modules.

44. The method according to claim 34, further comprising:

conducting a transillumination scan by maintaining said radiation beam and an object to be scanned stationary; and moving said collimator structure and the sensor assembly in a synchronized manner.

* * * * *